US009593397B2

(12) United States Patent
Imwinkelried et al.

(10) Patent No.: US 9,593,397 B2
(45) Date of Patent: Mar. 14, 2017

(54) MAGNESIUM ALLOY WITH ADJUSTABLE DEGRADATION RATE

(71) Applicant: DePuy Synthes Products, Inc., Raynham, MA (US)

(72) Inventors: Thomas Imwinkelried, Oberdorf (CH); Stefan Beck, Oberdorf (CH); Peter Uggowitzer, Ottenbach (CH); Joerg Loeffler, Greifensee (CH)

(73) Assignee: DePuy Synthes Products, Inc., Raynham, MA (US)

( * ) Notice: Subject to any disclaimer, the term of this patent is extended or adjusted under 35 U.S.C. 154(b) by 117 days.

(21) Appl. No.: 14/203,950

(22) Filed: Mar. 11, 2014

(65) Prior Publication Data
US 2014/0261911 A1 Sep. 18, 2014

Related U.S. Application Data

(60) Provisional application No. 61/783,554, filed on Mar. 14, 2013.

(51) Int. Cl.
| | |
|---|---|
| *C22C 23/04* | (2006.01) |
| *C22F 1/06* | (2006.01) |
| *C22C 23/02* | (2006.01) |
| *A61L 31/02* | (2006.01) |
| *A61L 31/14* | (2006.01) |

(52) U.S. Cl.
CPC ............ *C22C 23/04* (2013.01); *A61L 31/022* (2013.01); *A61L 31/148* (2013.01); *C22C 23/02* (2013.01); *C22F 1/06* (2013.01); *A61L 2400/12* (2013.01)

(58) Field of Classification Search
CPC . C22C 23/04; C22C 23/00; C22F 1/06; A61F 2/02
See application file for complete search history.

(56) References Cited

U.S. PATENT DOCUMENTS

| | | | | |
|---|---|---|---|---|
| 3,320,055 | A * | 5/1967 | Foerster .................. | C22C 23/00 148/420 |
| 2008/0031765 | A1 | 2/2008 | Gerold et al. | |
| 2012/0095548 | A1 | 4/2012 | Gregorich | |
| 2013/0144290 | A1* | 6/2013 | Schiffl ..................... | C22C 23/04 606/62 |
| 2014/0065009 | A1* | 3/2014 | Imwinkelried .......... | A61L 27/58 420/405 |
| 2015/0129091 | A1* | 5/2015 | Mueller .................... | C22F 1/06 148/538 |
| 2015/0129092 | A1* | 5/2015 | Mueller .................. | C22C 23/04 148/538 |
| 2016/0022876 | A1 | 1/2016 | Imwinkelried et al. | |

FOREIGN PATENT DOCUMENTS

| | | |
|---|---|---|
| CN | 1743486 | 3/2006 |
| CN | 1792384 | 6/2006 |
| CN | 101629260 | 1/2010 |
| CN | 101658691 | 3/2010 |
| CN | 101899600 | 12/2010 |
| DE | 1483204 A1 | 10/1969 |
| EP | 1959025 | 8/2008 |
| WO | WO 2004/013364 | 2/2004 |
| WO | WO 2009/147861 A1 | 12/2009 |
| WO | WO 2012/003522 | 1/2012 |
| WO | WO 2013/107644 | 7/2013 |
| WO | WO 2014/001321 | 1/2014 |

OTHER PUBLICATIONS

Zhang et al., "Research on an Mg—Zn Alloy as a Degradable Biomaterial", Acta Materialia, Jun. 10, 2010, No. 6, 626-640.
Zhang et al., "Enhanced Mechanical Properties in Fine-Grained Mg-1,ozn-0.5Ca Alloys Prepared by Extrusion at Different Temperatures", Scripta Materialia, Nov. 1, 2010, vol. 63, No. 10, 1024-1027.
Oh-Ishi et al., "Age-Hardening Response of Mg-0.3at.%Ca Alloys With Different Zn Contents", Materials Science and Engineering, Nov. 25, 2009, vol. 526, No. 1-2, 177-184.
Oh et al., "TEM and 3DAP Characterization of an Age-Hardened Mg—Ca—Zn Alloy", Scripta Materialia, Sep. 1, 2005, vol. 53, No. 6, 675-679.
Somekawa et al., "High Strength and Fracture Toughness Balance on the Extruded Mg—Ca—Zn Alloy", Materials and Engineering, Apr. 20, 2007, vol. 459, No. 1-2, 366-370.
Oh-Ishi et a., "Influence of Zn Additions on Age-Hardening Response and Microstructure of Mg-0.3at% Ca Alloys", Magnesium Technology 2010, Proceedings of a Symposium Held During TMS Annual Meeting & Exhibition, Jan. 1, 2010, 517-520.
Li et al., "Microstructure, Mechanical Properties and Corrosion Behavior of Mg—1Zn—0.5Ca Alloy", Advanced Materials Research, Jan. 1, 2011, vol. 311-313,1735-1740.
Yang et al., "Comparison of As-Cast Microstructures and Solidification Behaviours of Mg—Zn—Al Ternary Magnesium Alloys With Different Zn/Al Mass Ratios", Advanced Materials Research, Jan. 1, 2012, vol. 548, 322-324.
Witte et al., "Degradable Biomaterials Based on Magnesium Corrosion", Curr. Opin. Solid State Mater., Sci, Aug. 2008, 12, 63-72.
Staiger et al., "Magnesium and its Alloys as Orthopedic Biomaterials: A Review", Biomaterials, Oct. 2006, 27, 1728-1734.

(Continued)

*Primary Examiner* — Veronica F Faison
(74) *Attorney, Agent, or Firm* — Baker & Hostetler LLP

(57) ABSTRACT

An alloy and an implant having a three-dimensional structure based on such alloy. The alloy comprises a MgZnCa alloy containing nanosized precipitates being less noble than the Mg matrix alloy and having a Zn content ranging 0.1 wt. % Zn to 2 wt. % Zn and a calcium content ranging from 0.2 wt. % to 0.5 wt. %, and having less than 0.04 wt. % of one or more other elements with the remainder being Mg. For these micro-alloys, any second phase generated during the solidification process can be completely dissolved by a solution heat treatment. Finely dispersed nanosized precipitates can then be generated by a subsequent aging heat treatment step. These precipitates are used to "pin" the grain boundaries and to prevent the coarsening of the grain structure during further processing to achieve grain sizes below 5 μm.

19 Claims, No Drawings

(56) References Cited

OTHER PUBLICATIONS

Zberg et al., "MgZnCa Glasses Without Clinically Observable Hydrogen Evolution for Biodegradable Implants", Nat. Mater., Nov. 2009, 8, 887-891.
Hanzi et al., "Design Considerations for Achieving Simultaneously High-Strength and Highly Ductile Magnesium Alloys", Philos, Mag. Lett., Sep. 2012, 92, 417-427.
Tapiero et al., "Trace Elements in Human Physiology and Pathology: Zinc and Metallothioneins", Biomed. Pharmacother., Mar. 2003, 57, 399-411.
Stefanidou et al., "Zinc: A Multipurpose Trace Element", Arch. Toxicol., Sep. 2006, 80, 1-9.
Gunde et al., "High-Strength Magnesium Alloys for Degradable Implant Applications", Mater. Sci. Eng. A, Sep. 2011, 528, 1047-1054.
Hanzi et al., "Design Strategy for Microalloyed Ultra-Ductile Magnesium Alloys", Philos. Mag. Lett., Jun. 2009, 89, 377-390.
Koike, "Dislocation Plasticity and Complementary Deformation Mechanisms in Polycrystalline Mg Alloys", Mater. Sci. Forum, Mar. 2004, 449-452, 665-668.
Koike et al., "The Activity of Non-Basil Slip Systems and Dynamic Recovery at Room Temperature in Fine-Grained AZ31B Magnesium", Acta Mater., Apr. 2003, 51, 2055-2065.
Mendis et al., "Precipitation-Hardenable Mg—2.4Zn—0.1Ag—0.1Ca—0.16Zr (at.%) Wrought Magnesium Alloy", Acta Mater., Feb. 2009, 57, 749-760.
Homma et al., "Effect of Zr addition on the Mechanical Properties of As-Extruded Mg—Zn—Ca—Zr Alloys", Mater. Sci. Eng. A, Apr. 2010, 527, 2356-2362.
Kraus et al., "Magnesium Alloys for Temporary Implants in Osteosynthesis: In Vivo Studies of Their Degradation and Interaction With Bone", Acta Biomater., Mar. 2012, 8, 1230-1238.
Pichler et al., "Immunological Response to Biodegradable Magnesium Implants", JOM, Feb. 5, 2014, 1-7.
Liu et al., "Calculated Phase Diagrams and the Corrosion of Die-Cast Mg—Al Alloys", Sci., Mar. 2009, 51, 602-619.
Bakhsheshi-Rad et al., "Relationship between the corrosion behavior and the thermal characteristics and microstructure of Mg—0.5Ca—xZn alloys," Corros, Sci., Jul. 2012, 64, 184-197.
Hanawalt et al., "Corrosion Studies of Magnesium and Its Alloys," Trans. AIME, Feb. 1942, vol. 147, 273-299.
Hillis et al., Paper presented at SDCE 14th International Die Casting Congress and Exposition, Toronto, Canada, Paper No. G-T87-003, May 1987, 1-7.
Song et al., "Corrosion Mechanisms of Magnesium Alloys", Adv. Eng. Mater., Sep. 1999, 1, 1, 11-33.
Song et al., "Understanding Magnesium Corrosion", Adv. Eng. Mater., Dec. 2003, 5, 12, 837-858.
Song et al., Paper presented at the Magnesium Technology Conference at TMS, New Orleans, LA, Feb. 2001, 255-262.
Schinhammer et al., "On the Immersion Testing of Degradable Implant Materials in Simulated Body Fluid: Active pH Regulation using CO2", Adv. Eng. Mater., Jun. 2013, 15, 6, 434-41.
Cao et al., "Corrosion of Ultra-High-Purity Mg in 3.5% NaCl Solution Saturated With Mg(OH)2", Corros. Sci., Jun. 2013, 75, 78-99.
Kalb et al., "Impact of Microgalvanic Corrosion on the Degradation Morphology of WE43 and Pure Magnesium Under Exposure to Simulated Body Fluid", Corros. Sci., Jan. 2012, 57, 122-130.
Hanzi et al., "On the In Vitro and In vivo Degradation Performance and Biological Response of New Biodegradable Mg—Y—Zn Alloys", Acta Biomater., May 2010, 6, 1824-1833.
Yamamoto et al., "Effect of Inorganic Salts, Amino Acids and Proteins on the Degradation of Pure Magnesium in Vitro", Mater. Sci. Eng. C, 2009, 29, Jun. 1559-1568.
Kirkland et al., "Assessing the Corrosion of Biodegradable Magnesium Implants: A Critical Review of Current Methodologies and their Limitations", Acta Biomater., Mar. 2012, 8, 925-936.
Kirkland et al., "Buffer-Regulated Biocorrosion of Pure Magnesium", J. Mater. Sci. Mater. Med., Feb. 2012, 23, 283-291.

Abidin et al., "Corrosion of High Purity Mg, Mg2Zn0.2Mn, ZE41 and AZ91 in Hank's Solution at 37 oC", Corros. Sci., Jul. 2011, 53, 3542-3556.
Abidin et al., "The In Vivo and In Vitro Corrosion of High-Purity Magnesium and Magnesium Alloys WZ21 and AZ91", Corros. Sci., Jun. 2013, 75, 354-366.
Song et al., "The Role of Second Phases in the Corrosion Behavior of Mg—5Zn Alloy", Corros. Sci.,Apr. 2012, 60, 238-245.
Cha et al., "Biodegradability Engineering of Biodegradable Mg Alloys: Tailoring the Electrochemical Properties and Microstructure of Constituent Phases", Scietif. Rep., Aug. 2013, 3, 1-6.
Bakhsheshi-Rad et al., "Characterization and Corrosion Behavior of Biodegradable Mg—Ca and Mg—Ca—Zn Implant Alloys", Appl. Mech. Mater., Jan. 2012, 121-126, 568-572.
Zhang et al., "Microstructure, Mechanical Properties and Bio-Corrosion Properties of Mg—Zn—Mn—Ca Alloy for Biomedical Application", Mater. Sci. Eng. A, Jun. 2008, 497, 111-118.
Du et al., "Effects of Zn on the Microstructure, Mechanical Property and Bio-Corrosion Property of Mg—3Ca Alloys for Biomedical Application", Mater. Chem. Phys., Feb. 2011, 125, 568-575.
Kirkland et al., "In-Vitro Dissolution of Magnesium-Calcium Binary Alloys: Clarifying the Unique Role of Calcium Additions in Bioresorbable Magnesium Implant Alloys", J. Biomed. Mater. Res. B Appl. Biomater., Oct. 2010, 95, 91-100.
Wilson et al., "Effects of Preferred Orientation on the Grain Size Dependence of Yield Strength in Metals", Philos. Mag., Jun. 1963, 8, 1543-1551.
Barnett et al., "Influence of Grain Size on the Compressive Deformation of Wrought Mg—3A1—1Zn", Acta Mater., Aug. 2004, 52, 5093-5103.
Gottstein et al., Grain Boundary Migration in Metals: Thermodynamics, Kinetics, Applications, Boca Raton FL, CRC Press, Taylor & Francis Group, 2010, 1-685.
Sudholz et al., "Electrochemical Properties of Intermetallic Phases and Common Impurity Elements in Magnesium Alloys", Electrochem, Solid-State Lett., Jun. 2011, 14(2), C5-C7.
Manohar et al., "Five Decades of the Zener equation", ISIJ Int., Mar. 1998, 38, 9, 913-924.
L'Ecuyer et al., "Precipitation Interactions With Dynamic Recrystallization of a HSLS Steel", Acta Metall., Apr. 1989, 37, 4, 1023-1031.
Li, et al., "Preparation and in vitro degradation of the composite coating with high adhesion strength on biodegradable Mg Zn Ca alloy," Materials Characterization, Elsevier, New York, NY, US, vol. 62, No. 12, Jul. 10, 2011, 1158-1165.
Wang et al., "Biocorrosion of coated Mg Zn Ca alloy under constant compressive stress close to that of human tibia," Materials Letters, North Holland Publishing Company, Amsterdam, NL., vol. 70, Dec. 2, 2012, 174-176.
International Search Report for International application PCT/US2013/057294 dated Jan. 31, 2014; 6 pages.
International Search Report for International application PCT/US2014/023047 dated Jun. 17, 2014; 16 pages.
Birbilis et al. "A Combined Neural Network and Mechanistic Approach for the Prediction of Corrosion Rate and Yield Strength of Magnesium-Rare Earth Alloys", Corrosion Science, 53 pp. 168-176, Jan. 2011.
Birbilis et al. "On the Corrosion on Binary Magnesium-Rare Earth Alloys", Corrosion Science, 51, pp. 683-689, Mar. 2009.
Chia et al. "The Effect of Alloy Composition on the Microstructure and Tensile Properties of Binary Mg-rare Earth Alloys" Intermetallics, 17, pp. 481-490, Jul. 2009.
Sudholz et al., "Corrosion Behaviour of Mg-alloy AZ91E With Atypical Alloying Additions", Journal of Alloys and Compounds, 471, pp. 109-115, Mar. 2009.
Mendis et al., "An Enhanced Age Hardening Response in Mg_Sn Based Alloys Containing Zn", Materials Science & Engineering, 435-436, pp. 163-171, Nov. 2006.
Hofstetter et al., "High-Strength Low-Alloy (HSLA) Mg—Zn—Ca Alloys with Excellent Biodegradation Performance" The Minerals, Metals & Materials Society, JOM, vol. 66, No. 4, pp. 566-572, Feb. 2014.

(56) References Cited

OTHER PUBLICATIONS

Shaw, "Corrosion Resistance of Magnesium Alloys", ASM Handbook, vol. 13A Corrosion: Fundamentals, Testing, and Protection, pp. 692-696, 2003.
Song, Control of Biodegradation of Biocompatable Magnesium Alloys, Corrosion Science 49, pp. 1696-1701, Feb. 2007.
Yu Sun et al., Preparation and characterization of a new biomedical Mg—Zn—Ca alloy, Materials and Design, vol. 34, pp. 58-64, Feb. 2012.

* cited by examiner

MAGNESIUM ALLOY WITH ADJUSTABLE DEGRADATION RATE

CROSS REFERENCE TO RELATED APPLICATIONS

This application claims the benefit of U.S. Provisional Application No. 61/783,554, filed on Mar. 14, 2013, the disclosure of which is hereby incorporated by reference in its entirety.

BACKGROUND OF THE INVENTION

Magnesium implants were clinically used for the treatment of bone fractures by several surgeons back in the 1930s. For instance, J. Verbrugge (1934) used both, pure magnesium and Mg-8% Al alloy implants on 21 patients. However, after the Second World War, the use of magnesium as a resorbable implant material fell into oblivion. In recent years, researchers have renewed their interest in resorbable magnesium implants. A main focus of magnesium research is the development of alloys and coatings. The major goals are to control the degradation rate, to avoid the formation of gas bubbles during degradation and to avoid potentially harmful alloying elements. Therefore, a need exists for magnesium alloys with a homogenous degradation behavior whose rate of degradation can be controlled and/or tuned as desired.

Commercial grade pure magnesium (3N—Mg) has poor mechanical properties in comparison with alloys like AZ91 or WE43. The possibilities to harden pure magnesium are quite limited. Hardening might be achieved by refining the grain microstructure using plastic deformation to induce dynamic recrystallization (e.g. by extrusion). The fine grained microstructure is not only necessary to achieve a better strength level but also needed to avoid mechanical anisotropy (strength difference between tension and compression). The microstructure might not be stable, though.

Embodiments of the present invention overcome one or more of above-noted challenges.

BRIEF SUMMARY OF THE INVENTION

The present disclosure provides several exemplary embodiments of the present invention, some of which are discussed below.

In an aspect, the present invention provides an alloy composition and an implant having a three-dimensional structure based on such alloy composition. In one embodiment, the alloy is substantially free of microgalvanic elements. In another embodiment, the composition comprises a MgZnCa alloy having a Zn content ranging from 0.1 wt. % Zn to 2 wt. % Zn and a calcium content ranging from 0.2 wt. % to 0.5 wt. %, less than 0.04 wt. % of one or more other elements located in a secondary phase, and with the remainder being Mg and containing nanosized precipitates being less noble than the Mg remainder. In another embodiment, the composition consists essentially of a MgZnCa alloy having a Zn content ranging from 0.1 wt. % Zn to 2 wt. % Zn and a calcium content ranging from 0.2 wt. % to 0.5 wt. %, less than 0.04 wt. % of one or more other elements located in a secondary phase and with the remainder being Mg and containing nanosized precipitates being less noble than a MgZn alloy. In another embodiment, the composition consists of a MgZnCa alloy having a Zn content ranging from 0.1 wt. % Zn to 2 wt. % Zn and a calcium content ranging from 0.2 wt. % to 0.5 wt. %, less than 0.04 wt. % of one or more other elements located in a secondary phase and with the remainder being Mg and containing nanosized precipitates being less noble than the surrounding Mg phase.

In some such embodiments, the less noble than Mg nanosized precipitates comprise $(Mg,Zn)_2Ca$. In other such embodiments, the nanosized precipitates being more noble than the Mg matrix comprise $Mg_6Zn_3Ca_2$.

In some embodiments of the alloy according to the present invention, the alloy has a grain size of: less than 10 µm; less than 5 µm. In some embodiments of the alloys of present invention, the alloy has a yield strength of at least 180 MPa. In one embodiment, the alloy has an ultimate tensile strength of at least 240 MPa. In another embodiment, the alloy has at least 10% elongation at break. In yet another embodiment, the alloy has an in vitro degradation rate of less than 0.5 $mg/cm^2$ day as measured in a simulated body fluid.

In other embodiments, the implant is an orthopedic implant. In such embodiments, the orthopedic implant comprises one or more of the following: a nail, a screw, a staple, a plate, a rod, a tack, a bolt, a bolt to lock a intramedullary ("IM") nail, an anchor, a dowel, a plug, a peg, a sleeve, a mesh, a transconnector, a nut, a shaped body, spinal cage, a wire, a K-wire, a woven structure, clamp, splint, scaffold, foam and honeycomb structure. In some other embodiments, the implant has a lower degradation rate compared to magnesium alloy implants containing microgalvanic impurities.

In other embodiments, the implant is a non-orthopedic implant. In such embodiments, the non-orthopedic includes a cardiovascular stent, a neuro stent and a vertebroplasty stent.

In yet another embodiment of the implant, each alloy has an in vitro degradation rate of less than 0.5 $mg/cm^2$ day as measured in a simulated body fluid.

In an aspect, the present invention provides a method of producing an alloy according to the embodiments described herein. In one embodiment, the method comprises: (a) casting a alloy containing (i) commercially pure magnesium having a purity of at least 99.96 wt. %; and (ii) from 0.1 to 2.0 wt. % zinc having a purity of at least 99.9 wt. % and (iii) from 0.2 to 0.5 wt % calcium having a purity of a least 99.9 wt %, said casting being performed in an inert atmosphere and an inert reaction vessel; (b) solution heat treat the cast alloy at two different temperatures wherein a first temperature is below an eutectic temperature of Mg—Zn and a second temperature is above the eutectic temperature of the ternary Mg—Zn—Ca system to thereby form a MgZnCa alloy containing from 0.1 wt. % Zn to 2 wt. % Zn and 0.2 wt % Ca to 0.5 wt % Ca (c) aging heat treatment between 100° C. and 300° C.; and (d) extruding the alloy into a desired shape. In some embodiments, the MgZnCa alloy is monophasic.

The impurity limits for the commercially pure magnesium are: Fe<30 ppm, Cu<20 ppm, Ni<5 ppm, Mn<200 ppm, Si<200 ppm whereas the total amount of these impurities should be below 400 ppm.

DETAILED DESCRIPTION OF THE INVENTION

Reference will now be made in detail to the various embodiments of the present disclosure. In one embodiment of the present invention, a MgZnCa alloy comprises a plurality of nanosized precipitates, and has a Zn content ranging from 0.1 wt. % Zn to 2 wt. % Zn, a calcium content ranging from 0.2 wt. % to 0.5 wt. %, has less than 0.04 wt. % of one or more other elements, with the remainder being Mg wherein the plurality of nanosized precipitates are less noble than the Mg remainder. In yet another embodiment, the MgZnCa alloy consists essentially of a plurality of nanosized precipitates, and has a Zn content ranging from 0.1 wt. % Zn to 2 wt. % Zn, a calcium content ranging from 0.2 wt. % to 0.5 wt. %, has less than 0.04 wt. % of one or more other elements, with the remainder being Mg, wherein the nanosized precipitates are less noble than the Mg remainder. In another embodiment, a MgZnCa alloy consists of a plurality of nanosized precipitates, and has a Zn content ranging from 0.1 wt. % Zn to 2 wt. % Zn, a calcium content ranging from 0.2 wt. % to 0.5 wt. %, with the remainder being Mg wherein the plurality of nanosized precipitates are less noble than the Mg remainder. In some such embodiments, the less noble than Mg nanosized precipitates are $(Mg,Zn)_2Ca$.

In another embodiment of the implant of the present invention, the implant has a three-dimensional structure and comprises a MgZnCa alloy. In an embodiment, the implant has a three-dimensional structure made from a MgZnCa alloy comprising a plurality of nanosized precipitates, has a Zn content ranging from 0.1 wt. % Zn to 2 wt. % Zn, a calcium content ranging from 0.2 wt. % to 0.5 wt. %, has less than 0.04 wt. % of one or more other elements, with the remainder being Mg, wherein the plurality of nanosized precipitates are less noble than the Mg remainder. In another embodiment, the implant has a three-dimensional structure and comprises a composition consisting essentially of a MgZnCa alloy containing a plurality of nanosized precipitates, has a Zn content ranging from 0.1 wt. % Zn to 2 wt. % Zn, a calcium content ranging from 0.2 wt. % to 0.5 wt. %, having less than 0.04 wt. % of one or more other elements, with the remainder being Mg and wherein the plurality of nanosized precipitates are less noble than the Mg remainder. In another embodiment, the implant has a three-dimensional structure and comprises a composition consisting of a MgZnCa alloy containing a plurality of nanosized precipitates, has a Zn content ranging from 0.1 wt. % Zn to 2.0 wt. % Zn, a calcium content ranging from 0.2 wt. % to 0.5 wt. %, has less than 0.04 wt. % of one or more other elements, with the remainder being Mg, wherein the plurality of nanosized precipitates are less noble than the Mg remainder. In such embodiments, the less noble nanosized precipitates comprise $(Mg,Zn)_2Ca$.

Generally, the Zn content in the various embodiments of the MgZnCa alloy and an implant based on the various embodiments of the MgZnCa alloy, according to the present invention, can be any suitable amount between 0.1 wt. % to 2 wt. %. In an embodiment, the MgZnCa alloy has Zn content which may be independently selected from ranges from 0.1 wt. % to 2 wt. %; 0.5 wt. % to 2 wt. %; 0.6 wt. % to 0.8 wt. %; 1 wt. % to 2 wt. %; 0.1 wt. % to 0.5 wt. %; 0.1 wt. % to 1 wt. %; and any subset of ranges set forth herein.

Generally, the Ca content in the various embodiments of the MgZnCa alloy and in an implant based on the various embodiments of the MgZnCa alloy, according to the present invention, can be any suitable amount between 0.2 wt. % to 0.5 wt. %. In an embodiment, the MgZnCa alloy has Ca content which may be independent selected from ranges from 0.2 wt. % to 0.5 wt. %; 0.2 wt. % to 0.3 wt. %; 0.5 wt. % to 0.5 wt. %; and 0.2 wt. % to 0.4 wt. %.

Generally, with the alloy compositions of the present invention are based on a material free of secondary phases which otherwise act as cathodic microgalvanic cells. To achieve the necessary purity level of the MgZnCa alloy embodiments described herein, the acceptable amount of other elements within the alloy is limited.

In one embodiment, the MgZnCa alloy, having a plurality of nanosized precipitates being less noble than a Mg alloy, contains less than 400 ppm of total other elements. In another embodiment, the MgZnCa alloy, having a plurality of nanosized precipitates being less noble than a Mg alloy, contains less than 200 ppm of total other elements. In yet another embodiment, the MgZnCa alloy, having a plurality of nanosized precipitates being less noble than a Mg alloy, contains less than 100 ppm of total other elements. In still yet another embodiment, the MgZnCa alloy, having a plurality of nanosized precipitates being less noble than a Mg alloy, contains less than 50 ppm of total other elements.

In such embodiments, the other elements include one or more of Fe, Cu, Ni, Co, Si, Mn, Al, Zr and P.

The impurity level is maintained at such levels to control the corrosion rate once an implant, based on such alloys, is place in the body. It is necessary to control the corrosion rate so that the implant possesses sufficient strength over a period of time to allow healing and so not to interfere with the healing process. Although the degradation by-products from the magnesium alloys of the present invention are non-toxic, as the metal corrodes the pH near the implant increases to a basic pH. Likewise, hydrogen gas produced during the corrosion process must be eliminated. In the case endovascular implants, these concerns are insignificant as the constant blood flow over the implant removes the hydrogen gas and other degradation by-products.

Generally, the rare earth content in the various embodiments of the MgZnCa alloys compositions used in an implant, according to the present invention is limited. In such embodiments, the rare earth elements include Sc, Y, the Lanthanide elements, atomic numbers ranging from 57-71 and the Actinide elements, atomic numbers ranging from 89-103. In one embodiment, the rare earth content is less than 10 ppm. In another embodiment, the rare earth content is less than 5 ppm.

In some embodiments, the alloy is substantially free of microgalvanic elements. For the purposes of this application "microgalvanic element" refers to an impurity or precipitate with a higher potential than the surrounding magnesium matrix (i.e. that are electrochemically more noble). For the purpose of this application, "substantially free" refers to the number of microgalvanic elements that is small enough not to change the overall degradation behavior of the alloy from a overall homogeneous degradation to a localized degradation.

The mechanical properties of the commercially pure magnesium are improved by solid solution hardening with high purity zinc without affecting the homogeneous nature of the alloy. A fine grained microstructure can be achieved by plastic deformation and stabilized with secondary phases which are less noble than the magnesium matrix. For example, the less noble $(Mg,Zn)_2Ca$ phase can be obtained by small additions of high purity calcium and adequate heat treatment. If needed, the degradation rate can be accelerated, while maintaining a uniform corrosion profile, by modification of the composition and the aging heat treatment to form fine $Mg_6Zn_3Ca_2$ precipitates.

Implants made from the compositions described herein have advantageous physical properties, including high yield strength, high ultimate tensile strength, and elongation at break. In some embodiments, each alloy has the yield strength of at least 180 MPa. In some embodiments, each alloy has the yield strength of at least 200 MPa. In other embodiments, each alloy has a yield strength of at least at least 2200 MPa. In some embodiments, each alloy has an ultimate tensile strength of at least 240 MPa. In other embodiments, each alloy has an ultimate tensile strength of at least 260 MPa, at least 280 MPa, at least 300 MPa, at least 320 MPa, at least 340 MPa, at least 360 MPa, or at least 380 MPa. In some embodiments, each alloy has at least 10% elongation at break. In other embodiments, each alloy has elongation at break values of: at least 12%, at least 14%, at least 16%, at least 18%, at least 20%, and at least 22%.

Implants according exemplary embodiments of the present invention also have advantageous chemical properties in vitro and in vivo. In some embodiments, each alloy has an in vitro degradation rate of less than 0.5 mg/cm$^2$day as measured in a simulated body fluid. In other embodiments, each alloy has an in vitro degradation rate of less than 0.05 mg/cm$^2$day, less than 0.1 mg/cm$^2$day, less than 0.15 mg/cm$^2$day, less than 0.2 mg/cm$^2$day, less than 0.25 mg/cm$^2$day, less than 0.3 mg/cm$^2$day, less than 0.35 mg/cm$^2$day, less than 0.4 mg/cm$^2$day, or less than 0.45 mg/cm$^2$day, as measured in a simulated body fluid.

Implantable medical devices based on the compositions described herein can be manufactured for a variety of medical/clinical applications, including replacing a missing biological structure, to support a damaged biological structure, or to enhance an existing biological structure. The composition of the implants and/or the surfaces of the implants that contact the body/body tissues can be varied depending on the particular application under consideration. Surgical implants can be manufactured for medical/clinical applications in the area of orthopedics, neurosurgery, among others. Non-limiting examples of surgical implants include: neurosurgical implants, e.g. hydrocephalus shunts and components; intracranial aneurysm clips; bone and joint replacements, e.g., partial and total hip joint prostheses and total knee joint prostheses; osteosynthesis and spinal devices, e.g., metal bone screws, metal bone plates, medullary pins, metallic skeletal pins and wires, and total intervertebral spinal disc prostheses; oral and maxillo facial surgery implants; and spinal and pelvic systems such as Universal Spine System, Harrington System, and conventional systems. Accordingly, surgical implants that can be manufactured based on the compositions described herein can include a wide range of products varying in composition as described herein, structural complexity and medical/clinical applications. As such, implants for use in accordance with exemplary embodiments of the present invention can vary in size, shape, and other physical and chemical characteristics depending upon the context of use.

In some embodiments, the implant is an orthopedic implant. In such embodiments, the orthopedic implant comprises one or more of the following: a nail, a screw, a staple, a plate, a rod, a tack, a bolt, a bolt to lock an IM nail, an anchor, a dowel, a plug, a peg, a sleeve, a mesh, a transconnector, a nut, a shaped body, spinal cage, a wire, a K-wire, a woven structure, clamp, splint, scaffold, foam and honeycomb structure. In some other embodiments, the implant has a lower degradation rate compared to magnesium alloy implants containing microgalvanic impurities.

In other embodiments, the implant is a non-orthopedic implant. In such embodiments, the non-orthopedic includes a cardiovascular stent, a neuro stent and a vertebroplasty stent.

In vitro degradation tests in simulated body fluid (SBF) show that a uniform degradation with extremely low degradation rate can be achieved when using such the microalloyed MgZnCa. However, these alloys have poor mechanical properties in comparison to alloys like WE43 if no particular measures are taken. This limitation, it has been discovered, could be overcome by strict control of the grain size during all processing steps including casting. The hardening of the alloy can be achieved by refining the grain microstructure using plastic deformation (extrusion, forging, equal channel angular compression etc.). In addition to achieving a better strength level, the fine grained microstructure was also found to avoid mechanical anisotropy (strength difference between tension and compression).

The present disclosure further provides for methods of making various embodiments of the MgZnCa alloy described herein. In one embodiment, the method includes the steps of: (a) casting a alloy containing (i) commercially pure magnesium having a purity of at least 99.96 wt. %; and (ii) from 0.1 to 2.0 wt. % zinc having a purity of at least 99.9 wt. % and (iii) from 0.2 to 0.5 wt % calcium having a purity of a least 99.9 wt %, said casting being performed in an inert atmosphere and an inert reaction vessel; (b) solution heat treat the cast alloy at two different temperatures wherein a first temperature is below an eutectic temperature of Mg—Zn and a second temperature is above the eutectic temperature of the ternary Mg—Zn—Ca system to thereby form a MgZnCa alloy containing from 0.1 wt. % Zn to 2 wt. % Zn and 0.2 wt % Ca to 0.5 wt % Ca (c) aging heat treatment between 100° C. and 300° C.; and (d) extruding the alloy into a desired shape. In some embodiments, the MgZnCa alloy is monophasic. In some embodiments, the method may further include the step of a second aging heat treatment of the shaped alloy to improve either strength or ductility of the alloy.

The impurity limits for the commercially pure magnesium are: Fe<30 ppm, Cu<20 ppm, Ni<5 ppm, Mn<200 ppm, Si<200 ppm whereas the total amount of these impurities should be below 400 ppm. (Mg,Zn)$_2$Ca is one of the few phases which are electrochemically less noble than pure magnesium.

Phase calculations of the MgZnCa alloy system have shown that a compositional window exists for low Zn and Ca contents where complete dissolution of the alloying elements is possible and no second phase, from the casting process, remains after a solution heat treatment. While not wishing to be bound by theory, it was believed that advantageous properties could result from a stable fine grained microstructure within the alloy and that such a microstructure could be obtained if the grain boundaries are pinned during the extrusion process. The pinning could be achieved by the presence of fine precipitates. Unexpectedly, it was found that an aging heat treatment, prior to extrusion, results in the formation of nanosized precipitates which are not visible under an optical microscope but which are large enough to prevent the grains from coarsening. Furthermore, as the precipitates are less noble than the magnesium matrix and have no 3-dimensional connectivity among themselves, the precipitates do not deteriorate the degradation performance of the alloy. The MgZnCa alloy system, having the less noble fine precipitates, exhibited fine grain sizes less than 5 μm after extrusion of the casting billet.

For example, with the addition of 0.1 wt. % to 2.0 wt. % Zn and 0.2 wt. % to 0.5 wt. % Ca to Mg, such finely dispersed precipitates can be created by an aging heat treatment following the initial solution heat treatment. The weight percentage of calcium and zinc can be adjusted to control the degradation rate of the alloy. If the degradation rate of the alloy is too slow and needs to be accelerated, Mg$_6$Zn$_3$Ca$_2$ precipitates can be formed by slightly changing the alloy composition. As an example, for a Mg alloy with 1 wt. % Zn and 0.35 wt. % Ca, mainly (Mg,Zn)$_2$Ca nanoparticles are precipitated by an aging heat treatment at 200° C. whereas for a Mg alloy with 1.5 wt. % Zn and 0.25 wt. % Ca, mainly Mg$_6$Zn$_3$Ca$_2$ nanoparticles precipitate at the same temperature.

The magnesium alloys in the exemplary embodiments described above have especially favorable properties for processing and for their later intended purpose in comparison with traditional magnesium alloys: the ductility of the magnesium alloys is greatly elevated. For purposes of the present disclosure, the term "ductility" (or toughness, deformation capacity) refers to the ability of a metallic material to undergo permanent deformation under sufficiently high mechanical loads before cracking occurs. This ability is of great importance for many construction parts because only a ductile material is capable of dissipating local mechanical stress peaks by undergoing permanent deformation without cracking and with simultaneous cold solidification. This aspect, in particular, makes it especially advantageous to use the inventive magnesium alloys as a material, for example, for biodegradable implants, in particular, biodegradable bone fixation implants. With a given material, the ductility depends on the temperature, the stress rate, the multi-axle character of the acting mechanical stress state and the environment. Characteristic values of ductility include, e.g., the elongation at break and necking, the notched impact strength and the fracture toughness as described elsewhere herein.

It will be appreciated by those skilled in the art that changes could be made to the exemplary embodiments shown and described above without departing from the broad inventive concept thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and features of the disclosed embodiments may be combined. Unless specifically set forth herein, the terms "a", "an" and "the" are not limited to one element but instead should be read as meaning "at least one".

It is to be understood that at least some of the descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the method does not rely on the particular order of steps set forth herein, the particular order of the steps should not be construed as limitation on the claims. The claims directed to the method of the present invention should not be limited to the performance of their steps in the order written, and one skilled in the art can readily appreciate that the steps may be varied and still remain within the spirit and scope of the present invention.

The invention claimed is:

1. A composition comprising:
a MgZnCa alloy containing nanosized precipitates, the alloy having a Zn content ranging from 0.1 wt. % Zn to 2.0 wt. % Zn and a calcium content ranging from 0.2 wt. % Ca to 0.5 wt. % Ca, less than 0.04 wt. % of one or more other elements and with the remainder of the alloy being Mg, wherein the nanosized precipitates are less noble than the remainder Mg.

2. The composition of claim 1, wherein the alloy contains less than 400 ppm of total other elements.

3. The composition of claim 2, wherein the one or more other elements comprise Fe, Cu, Ni, Co, Si, Mn, Al, Zr, P or any combination thereof.

4. The composition of claim 1, wherein the alloy is substantially free of microgalvanic elements.

5. The composition of claim 1, wherein the nanosized precipitates that are less noble than the remainder Mg comprise $(Mg,Zn)_2Ca$.

6. The composition of claim 1, further comprising nanosized precipitates that are more noble than the Mg remainder wherein said precipitates comprise $Mg_6Zn_3Ca_2$.

7. The composition of claim 1, wherein the alloy has a grain size of less than 5 µm.

8. The composition of claim 1, wherein the alloy has a yield strength of at least 180 MPa.

9. The composition of claim 1, wherein the alloy has an ultimate tensile strength of at least 240 MPa.

10. The composition of claim 1, wherein the alloy has at least 10% elongation at break.

11. An implant comprising the composition of claim 1.

12. The implant of claim 11, wherein the implant has an in vitro degradation rate of less than 0.5 mg/cm$^2$ day as measured in a simulated body fluid.

13. The implant of claim 11, wherein the implant is an orthopedic implant.

14. The implant of claim 13, wherein the orthopedic implant comprises a nail, a screw, a staple, a plate, a rod, a tack, a bolt, a bolt to lock and IM nail, an anchor, a dowel, a plug, a peg, a sleeve, a mesh, a transconnector, a nut, a shaped body, a spinal cage, a wire, a K-wire, a woven structure, a clamp, a splint, a scaffold, a foam, a honeycomb structure, or any combination thereof.

15. The implant of claim 11, wherein the implant is a non-orthopedic implant.

16. The implant of claim 15, wherein the non-orthopedic implant comprises a cardiovascular stent, a neuro stent, or a vertebroplasty stent.

17. The implant of claim 11, wherein the implant has a lower degradation rate compared to implants made from a magnesium alloy containing microgalvanic elements.

18. A method of producing the composition of claim 1, comprising the steps of:
(a) casting a mixture containing (i) magnesium having a purity of at least 99.96 wt. % and having less than 0.04 wt. % of one or more other elements; (ii) from 0.1 wt. % to 2.0 wt. % zinc having a purity of at least 99.9 wt. %; and (iii) from 0.2 wt. % to 0.5 wt. % calcium metal having a purity of at least 99.9 wt. %, said casting being performed in an inert atmosphere and an inert reaction vessel;
(b) solution heat treating of the cast alloy at two or more different temperatures wherein a first temperature is below an eutectic temperature of Mg—Zn and a second temperature is above an eutectic temperature of the ternary Mg—Zn—Ca system to thereby form a MgZnCa alloy containing from 0.1 wt. % Zn to 2 wt. % Zn, and a calcium content ranging from 0.2 wt. % Ca to 0.5 wt. % Ca, and having less than 0.04 wt. % of one or more other elements with the remainder being Mg;
(c) age heat treating between 100° C. and 300° C. to create dispersed nanosized precipitates; and
(d) extruding the alloy into a desired shape.

19. The method of claim 18, further comprising the step of:
second age heat treating of the shaped alloy to improve strength or ductility.

* * * * *